United States Patent [19]
del Cerro et al.

[11] Patent Number: 5,273,530
[45] Date of Patent: Dec. 28, 1993

[54] INTRARETINAL DELIVERY AND WITHDRAWAL INSTRUMENTS

[75] Inventors: Manuel del Cerro, Pittsford; Eliot Lazar, Buffalo, both of N.Y.

[73] Assignee: The University of Rochester, Rochester, N.Y.

[21] Appl. No.: 613,165

[22] Filed: Nov. 14, 1990

[51] Int. Cl.$^5$ .............................................. A61M 31/00
[52] U.S. Cl. ............................................ 604/51; 604/117
[58] Field of Search ............... 128/749, 750, 758, 760, 128/763, 766, 770; 604/43, 44, 51, 117, 118; 606/4, 13-16

[56] References Cited

U.S. PATENT DOCUMENTS

| | | | |
|---|---|---|---|
| 1,125,887 | 1/1915 | Schimmel | 604/117 |
| 3,636,940 | 1/1972 | Gravlee | 128/750 |
| 3,735,751 | 5/1973 | Katz | 128/750 |
| 3,982,541 | 9/1976 | L'Esperanes | 606/4 |
| 4,714,464 | 12/1987 | Newton | 604/118 |
| 4,759,746 | 7/1988 | Straus | 604/51 |

FOREIGN PATENT DOCUMENTS

| | | | |
|---|---|---|---|
| 0496458 | 10/1950 | Belgium | 604/44 |
| 1052232 | 11/1983 | U.S.S.R. | 606/4 |

*Primary Examiner*—Max Hindenburg
*Attorney, Agent, or Firm*—Cooper & Dunham

[57] ABSTRACT

An intraretinal delivery and withdrawal instrument which has (a) a curved, distal frame for insertion into an orbit, which insertion is effected (i) inferior to the supraorbital ridge, (ii) superior to the eye, and (iii) in a caudal direction so as to reach the retina; (b) a tip for penetration into the subretinal region of the eye connected to the frame; and (c) an adjustable collar connected to the tip which collar is capable of being positioned so that the collar regulates the depth of tip penetration into the subretinal region including methods for uses thereof.

17 Claims, 5 Drawing Sheets

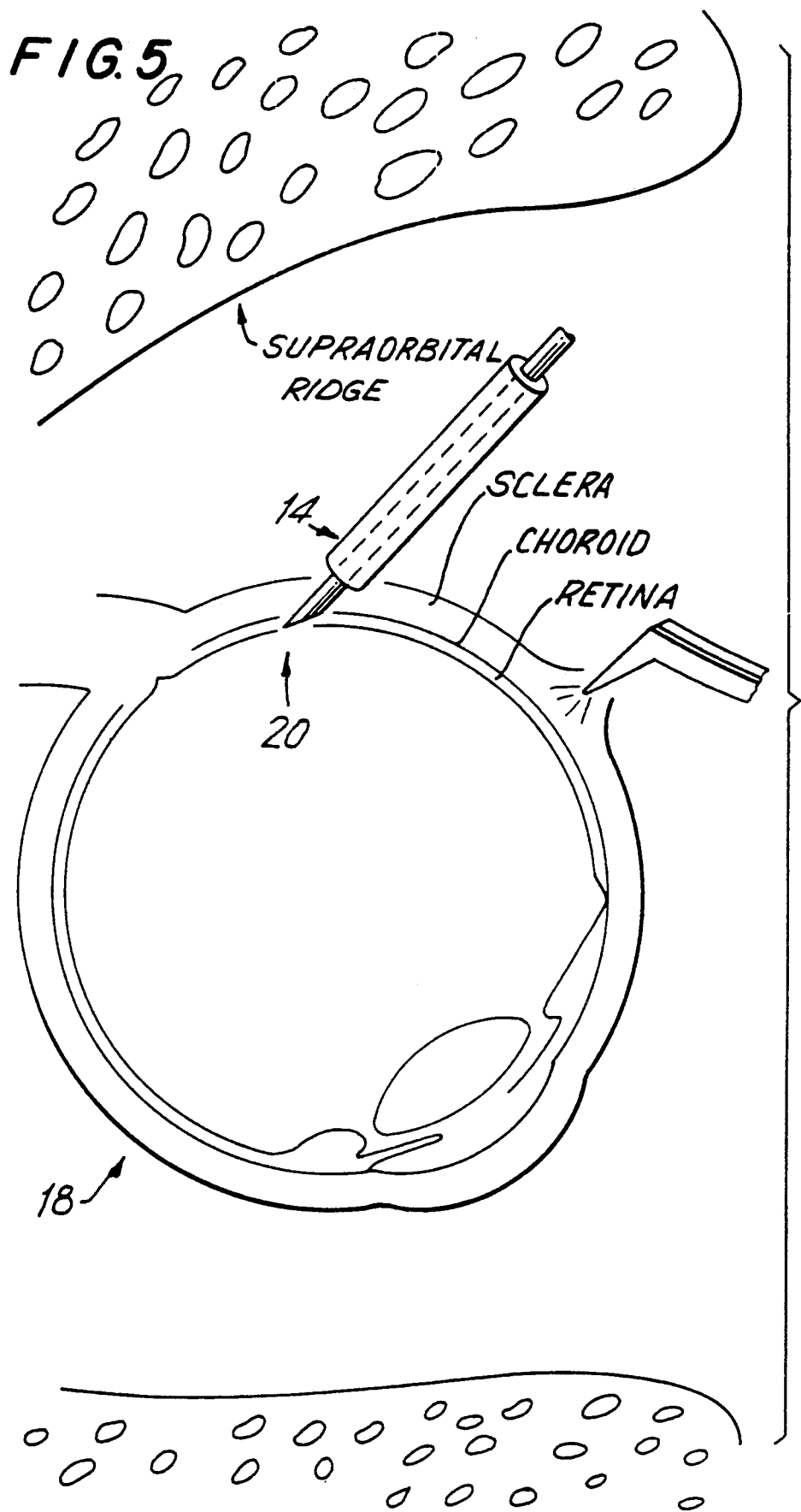

INTRARETINAL DELIVERY AND WITHDRAWAL INSTRUMENTS

BACKGROUND AND SUMMARY OF THE INVENTION

The invention is in the field of medical devices for intraocular sample delivery and withdrawal. More particularly, it pertains to instruments shaped and dimensioned for insertion into the orbit along an insertion path which extends along the periphery of the eye in a posterior direction to place the instrument tip adjacent posterior portions of the eye such as the sclera, choroid, the retina, or vitreous chamber.

Throughout this application various publications and patents are referenced and citations are provided in parentheses for them. The disclosures of these publications in their entireties are hereby incorporated by reference into this application to describe more fully the state of the art to which this invention pertains.

The remarkable efficiency of the eye as an organ for vision results from its highly specialized organization and the complicated coordination of its component parts which are vital to the process of normal vision. Damage to any essential structure can result in impairment of vision. Accordingly, it is particularly important that instruments designed for use in or around the eye (ocular globe) to aid in treatment or diagnosis of visual impairment must be safe and reliable, while at the same time permitting access to regions of the eye that are not easily accessible.

A common feature of known prior art intraocular transplantation instruments is that they carry out sample delivery by penetrating an anterior part of the eye, i.e. via a transcorneal or transscleral route, which creates the risks of corneal ulceration, cataract formation, and other anterior penetration problems. One exemplary prior art instrument is a microspatula which administers cells to the eye through a trans-scleral or trans-corneal surgical incision (12). Another exemplary prior art instrument is a glass micropipet which replaces cells in the retina by entering the eye anteriorly through an incision via the scleral route (10). Yet another exemplary instrument is a glass micro canula which effects transplantation of cells into the retina by entering the eye anteriorly through a surgical incision via a trans-scleral or trans-corneal route.

Known prior art instruments do not directly effect entry into the eye. Instead, an entry portal, i.e. a surgical incision, is believed to be necessary. Surgery involves inherent risks and possible complications such as vitreous loss, cataract formation, and intraocular infection. Of course, any instrument which requires surgical procedures before it could be used is less desirable than instruments which do not. Further, because such prior art instruments effect entry through surgical incisions, any attempts to implant at multiple sites within the eye can be exceedingly difficult and dangerous.

In contrast, the subject invention provides instruments which can enter the eye directly, without requiring a surgical incision as a prerequisite. Importantly, the subject invention makes it possible to transplant at multiple sites within the eye without the undesirable risks and consequences of multiple surgical procedures.

Further, in contrast to the prior art instruments, the subject invention provides a particularly effective way to control the depth of intraocular penetration. One embodiment of the invention uses a uniquely shaped and positioned adjustable collar to regulate the depth to which the instrument tip may enter the intraocular area. In contrast, it is believed that known prior art instruments cannot be pre-set to penetrate only to a pre-determined desired depth; instead, the penetration depth into the intraocular area is determined at the time of penetration. These instruments do not have the advantage of effecting intraocular penetration at a predetermined depth. This feature is believed to be particularly important because the ability to limit the actual penetration depth of an intraocular instrument could alleviate or eliminate important disorders or symptoms that can be associated with intrusion into the intraocular area. Another important benefit is the invention's ability to have a pre-set or predetermined depth of penetration into the eye, is that sample delivery or withdrawal can be pinpointed at the desired part of the eye, e.g. only the scleral area, the choroid area, the sub-retinal area the retinal area, or the vitreous area, etc.

The known prior art instruments typically provide sample delivery but not sample withdrawal with the same instrument. Further, it is believed that the known prior art instrument cannot be effectively pre-set to dispense only a desired volume but rather dispense the sample according to the pressure exerted by, or movement of, the operator at the time of sample delivery, i.e. sample size is not predetermined and dispensed before the instrument is in the eye. Accordingly, prior to the procedure of eye penetration, there is an effective way to be sure that only a predetermined amount of sample will in fact be administered to or withdrawn from the intraocular area.

The invention is believed to provide a new and reliably reproducible means for retinal transplantation without a surgical procedure on the eye as a prerequisite. In contrast, the known literature proposes techniques for intraretinal transplantation which require surgically opening the eye. Lopez, et al. (10) discuss a technique which required making a pars plana incision and inserting a micropipette through the globe into the subretinal space.

The method described by Lopez involves forming a retinal detachment in order to properly place the transplant. They note that "there are a number of potential pitfalls associated with this technique" and remark that the host epithelium must first be detached. This is a procedure which in the case of the human eye can be associated with subretinal neovascularization. In addition they note that "it may be difficult to be certain that no cells enter the vitreous cavity."

The technique proposed by Sheedlo et al. (11) requires excision of the superior rectus muscle, followed by an incision into the globe with a blade which penetrates the sclera and choroid to expose the subretinal space, prior to performing the transplantation of cells into this locus. Following the injection of material, the incision must be closed surgically with suture material.

Silverman and Hughes (12) report a technique which also involves a preliminary ocular incision prior to implantation of tissue. They propose a trans-corneal approach to the subretinal space which involves making a transverse incision through the cornea and then traversing the entire globe in order to reach the posterior pole.

BRIEF DESCRIPTION OF THE DRAWINGS

FIG. 5 illustrates a prior art technique for rotating the eye so that a posterior portion can be accessed but also illustrates access into a posterior portion of the eye using an instrument tip which can deliver or withdraw a predetermined amount of material in accordance with a feature of the invention.

DETAILED DESCRIPTION OF THE INVENTION

Figure 1:
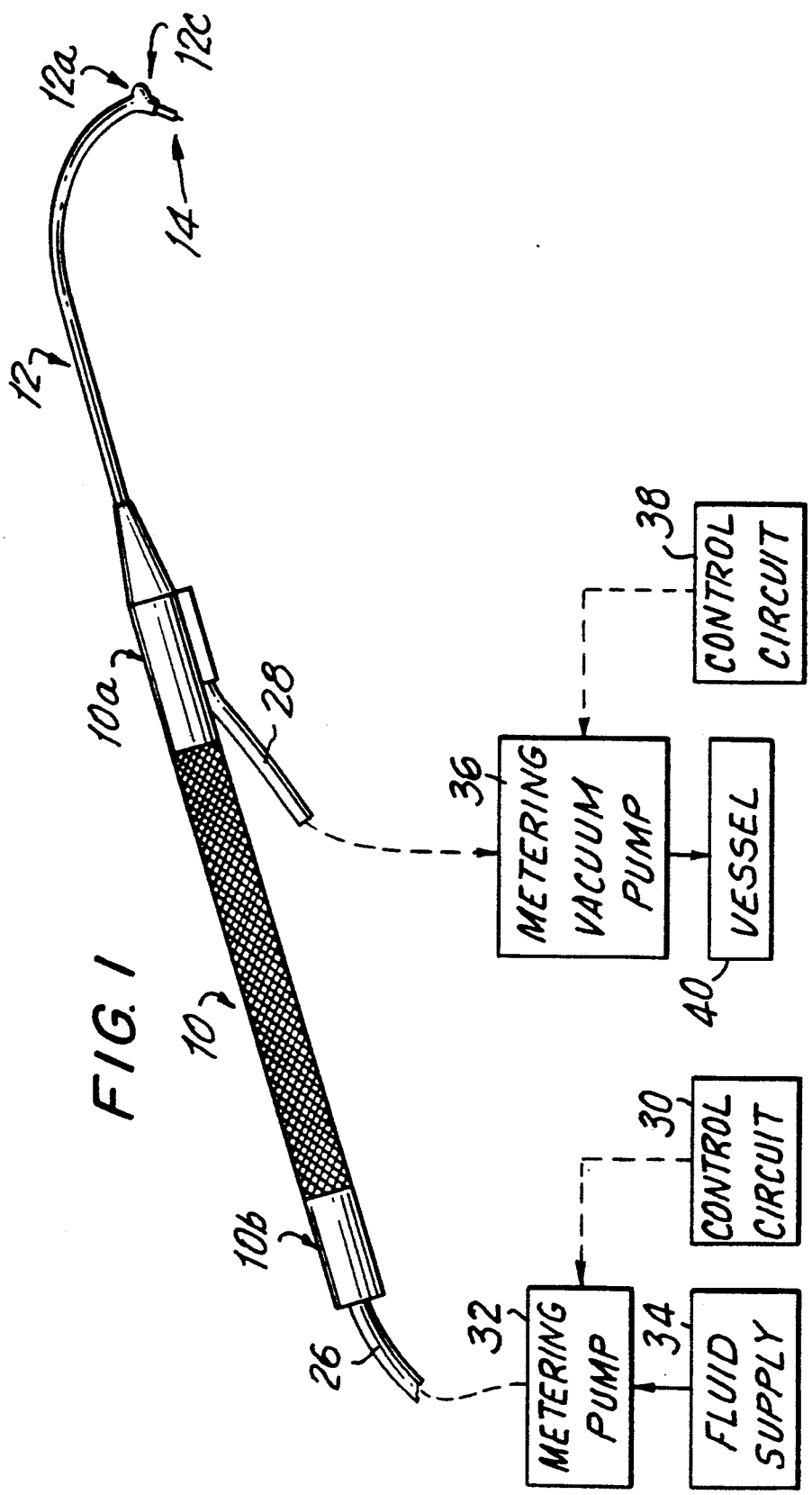
FIG. 1 illustrates a sample delivery and withdrawal instrument in accordance with an exemplary embodiment of the invention.
Figure 2:
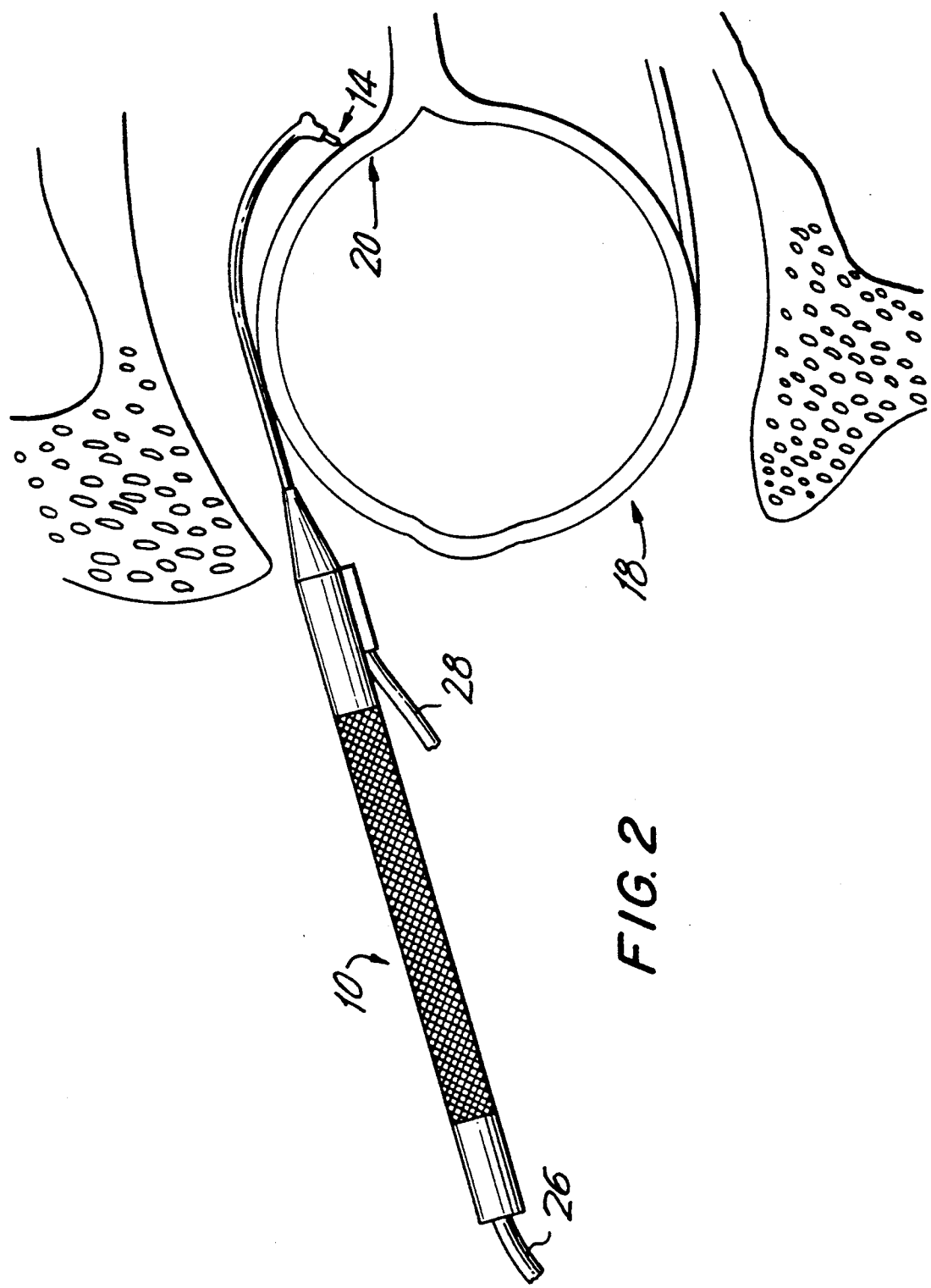
FIG. 2 illustrates access to a posterior portion of the eye using the instrument of FIG. 1.

Referring to FIGS. 1–4a, an exemplary instrument for withdrawal and delivery of a sample from and to a posterior part of the eye, has an elongated handle 10 having a distal end 10a and a proximal end 10b. Handle 10 is shaped and dimensioned to be grasped by the hand of the user carrying out the procedure of withdrawal or delivery of a sample from or to a posterior part of the eye. The instrument further comprises an elongated and curved frame 12 extending from the distal end 10a of handle 10. Frame 12 has a distal end 12a to which a tip 14 is attached. Frame 12, or at least the distal part thereof, and tip 14 are shaped and dimensioned for insertion into an eye orbit along an insertion path 16 (FIG. 2) which extends along the periphery of eye 18 so as to place tip 14 adjacent to the retinal or subretinal region 20 and in the direction for penetration into the subretinal region of the eye when said tip 14 is moved generally in the medial direction by manipulating handle 10. A scleral depressor 12c can extend from the distal tip of frame 12, e.g., at an angle of about 45 degrees to each of tip 14 and the adjacent part of frame 12, away from tip 14, to facilitate insertion of the frame along an insertion path around the periphery of the eye.

Handle 10 and the curved distal frame 12 can be made of a metal such as titanium, stainless steel, tantalum, or vitallium, or can be made of other suitable materials. Alternatively, handle 10 and the curved distal frame 12 can be made of a plastic material such as a polyethylene type plastic. Tip 14 can comprise a needle tip 22 which is made up of a metal such as titanium, stainless steel, tantalum, or vitallium, or some other suitable material, and an adjustable collar 24 (FIGS. 3a–4b) which regulates the depth to which tip 14 penetrates the eye, e.g., subretinal region 20 of the eye. Needle tip 22 can be the tip of a needle such as a 30 gauge or a 27 gauge needle, and extends at an angle such as a right angle to the distal end 12a of frame 12. In general, a needle tip in the range from about 32 gauge to 15 gauge would be suitable, depending on the particular patient and procedure, and depending on the physician's preference and needs.

Figure 3A:
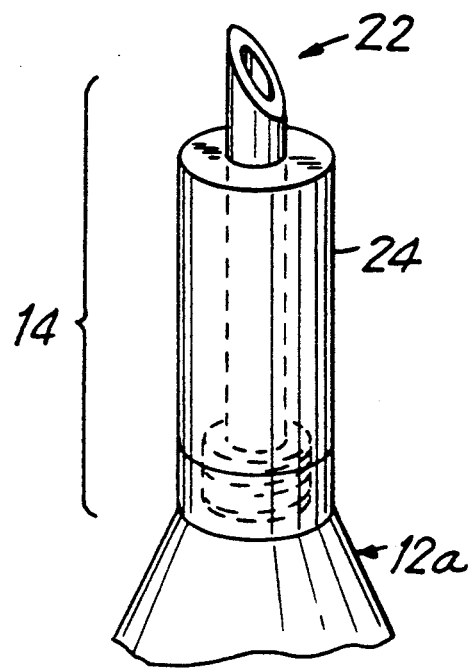
FIGS. 3a and 3b illustrate in more detail the tip end of the instrument of FIG. 1 and the way the tip is mounted.
Figure 3B:
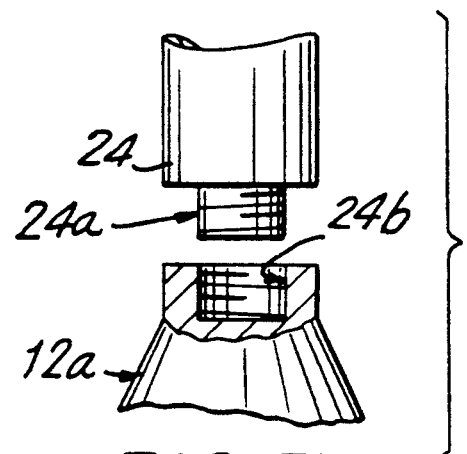
Figure 4A:
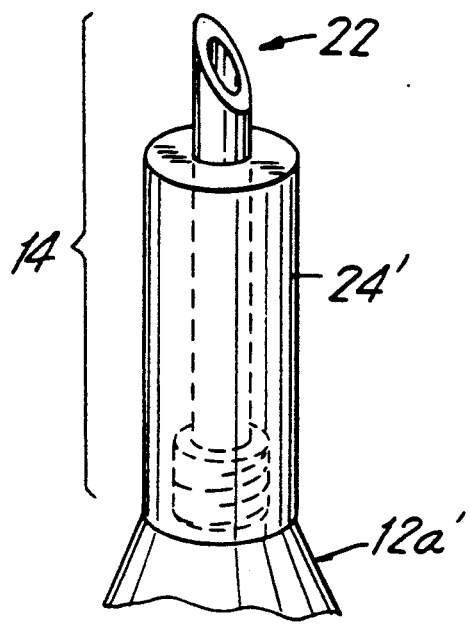
FIGS. 4a and 4b illustrate an alternate way of mounting the instrument tip.
Figure 4B:
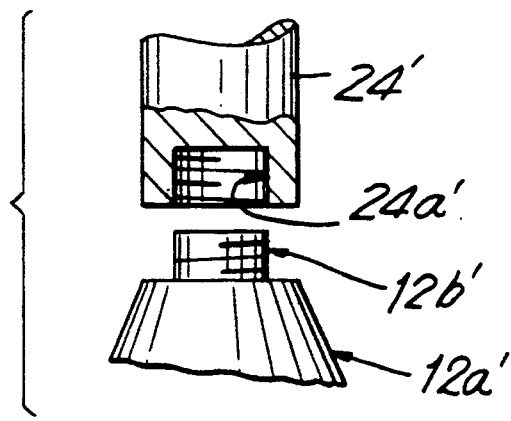

In the example of FIGS. 3a and 3b, distal end 12a tapers into a free end terminating into a central opening 12b provided with an internal screw thread mating with an external screw thread 24a which is at one end of adjustable collar 24. Further, the degree to which needle tip 22 penetrates the eye can be varied by adjusting the extent to which thread 24a is screwed into thread 12b. In one embodiment of the invention, adjustable collar 24 is a plastic sleeve. In another, it is a metallic adjustable sleeve of the same or similar shape. While it is believed that a sufficient range of penetration depth can be provided only by the degree to which threads 24a and 12b are screwed into each other, sleeves of different lengths may be used to extend the range. Interchangeable sleeves of different lengths or shapes can be used for other purposes as well, e.g., to accommodate special needs or preferences of the physician and/or of the patient. Instead of using mating threads, different sleeves that snap on or are frictionally or otherwise engaged can be used. As seen in FIGS. 4a and 4b, an alternative to the embodiment of FIGS. 3a and 3b is to have an internal thread 24a' at one end of sleeve 24' and an external thread 12b' at the distal end 12a' of the instrument frame.

In order to deliver or withdraw material from the eye, needle tip 22 is hollow and communicates with a passage through frame 12 which in turn communicates with a passage through handle 10. The passage through handle 10 in turn communicates with a feed line 26 and an aspiration line 28. Feed line 26 is in selective fluid flow communication with said hollow passage through handle 10 to deliver fluid to the eye through needle tip 22. To effect the delivery of a predetermined quantity of fluid into the eye, a control circuit 30 generates a delivery command signal, e.g., in response to the manual operation of a switch (not shown) to drive a metering pump 32 which pumps into feed line 26 the desired amount of fluid. A fluid supply 34 supplies the fluid to metering pump 32. To aspirate fluid from the eye, aspiration line 28 is in selective fluid flow communication with a metering vacuum pump 36 which, in response to a similarly generated aspiration command signal from control circuit 38, pumps out the desired quantity of fluid from the eye into a vessel 40. Of course, if desired, the instrument can be only for delivery of fluid to the eye, or only for aspiration of fluid from the eye, in which case it would have only feed line 26, and the associated components used for fluid delivery, or only aspiration line 28, and its associated components used for aspiration. Feed line 26 and aspiration line 28 can be made up of plastic or metal, but plastic feed and aspiration lines are currently preferred.

Referring to FIG. 5, a tip similar to that illustrated in FIGS. 3a and 3b, or in FIGS. 4a and 4b, which can conveniently regulate the depth of penetration into the eye, can be used in an otherwise prior art technique in accessing a posterior portion of the eye in the illustrated manner.

Various modifications of the disclosed apparatus are possible. For example, while electrically operated and electronically controlled metering pumps 32 and 36 can be used as discussed above, in an alternate structure, it is possible to use manually operated, syringe-type delivery and aspiration tools instead.

In an exemplary procedure in accordance with the invention, donor cells were implanted as follows. Second trimester human embryonic retinal cells obtained from electively aborted embryos age 13 to 17 weeks were used as donor tissue. Procurement of donor cells was in accordance with scientific and ethical guidelines which included institutional review and approval of the experimental protocol. In all cases, maternal consent was given only after the decision to have an elective abortion was made. The cells were prepared as follows. The eyes were obtained less than one hour after fetal death and collected in either calcium - magnesium medium or in human plasma at 4° C. Operating with the aid of a surgical microscope, the eyes were dissected open. The retinas were cleanly cut away, free of contamination from either vitreous or retinal pigment epithelium. Isolated retinas were trimmed into small fragments using a Vannas scissor (Storz, St. Louis, Mo.), and then placed into ice cold medium. Mechanical dissociation was used to obtain suspension of retinal cells and cell clusters. The dissociation was achieved by aspirating the retinal fragments through butterfly tubing (Abbott Hospitals, North Chicago, Ill.) and then releasing them through the same needle. By varying the needle gauge and the number of aspiration ejected cycles it was possible to maintain fine control over the final degree of dissociation. For example, a nearly pure single cell suspension is achieved by 2 cycles through a 30 gauge needle, while 1 cycle through a 27 gauge needle yields a suspension formed by clumps comprising a few hundred cells, as well as a negligible number of single cells. Hosts and anaesthesia were used as follows. Young male adult rats of the Wistar strain served as hosts. In experiments using rats, two to three groups of six rats each were used per experiment. The animals were anaesthetized with a mixture of chloral hydrate and sodium pentobarbital (Chloropent, Henry Schem Inc. Port Washington, N.Y.) at a dose of 3 ml/Kg. Topical 1% Alcaine drops (Propaine Hydrochloride, Alcon, Fort Forth, Tex.) were also used as a topical anaesthetic. The eyes were dilated pre-operatively with one drop each of 1% neo-synephrine and 1% mydriacyl (Alcon, Fort Worth, Tex.). The following delivery system and transplantation procedure were used. For most experiments, a 27 gauge needle tip, tightly sheathed in plastic, with 1.2-1.4 mm of the needle tip left exposed, was connected to a microliter syringe (Series 1700, Hamilton, Reno, Nev.), prior to the procedure (FIG. 1). The plastic collar placed on the needle serves as an adjustable regulator. By setting it at the appropriate depth, depending on the animal model being used, the collar serves to limit the depth of penetration and provides protection against over penetration. The plastic collar can be regulated so that only enough of the needle tip is exposed to reach the subretinal space without actually penetrating the retina. A major advantage of a tip connected to a plastic collar during injection into the retinal area is the prevention of large retinal holes or tears. Specifically in this example, minimal over-penetration of the tip cause part of the open portion of the bevel to be in the vitreous area, thereby leading to an intravitreal injection. The microliter syringe was preloaded with a suspension of neuroretinal cells. After the animal was appropriately anesthetized, collibri forceps (Storz, St. Louis, Mo.) were used to firmly grasp the sclera at the limbus and rotate the globe anteriorly. Then, using a stereo microscope for direct visualization, the needle was manually inserted through the sclera and gently rotated until the tip could be directly viewed through the retina, then the tip was advanced further so as to slightly elevate the retina. The plastic protective sheath prevents overpenetration of the needle and perforation of the neuroretina. With the bevel of the needle facing the globe, i.e. the ocular globe, the injection of cells was made. Following the injection, the needle was quickly withdrawn and the procedure repeated at a point 180° degrees opposite to the first injection site in the same eye. Typically, two micro-injections were made into the equatorial region of each eye. One was made superiorly at the 12 o'clock position and the other at the 6 o'clock position inferiorly. However, as many as four penetrations have been performed in a single rat eye and up to six into the lower hemisphere of the monkey eye. The needle was quickly withdrawn following each injection. After the experiment was completed a topical lubricant was placed on the cornea to prevent drying. Control injections were used as follows. In order to obtain instant, permanent and multilevel visualization of the spread of the injected fluid, colloidal carbon (3,4) was used to perform control injections in the identical manner as those involving injections of cell suspensions. One group of six animals served as the control group receiving colloidal carbon injections. Colloidal carbon (Biological India Inc., Pelikan, West Germany) was prepared in a 1:4 dilution with saline. In vivo exams were used as follows. All surgery was performed using an Olympus SZH stereomicroscope fitted with a 35 mm photographic camera as well as a videotaping apparatus. The same set up was used to photograph the transplants at various stages of growth. For the latter purpose, either a lensing system or a slide was used in order to bring the retina into fine focus. Indirect and direct ophthalmoscopy was routinely performed on all the transplant recipients. Using a Keeler (Keeler, Broomall, Pa.) indirect ophthalmoscope and a Volk Pan Retinal lens (Keeler, Broomall, Pa.) the animals were examined at regular intervals. This allowed us to constantly monitor the growth and condition of the transplant. Photographs were taken through the microscope using a Nikon camera or a Kowa camera in conjunction with the indirect ophthalmoscope.

The survival times and histological procedures were as follows. Survival times for the animals receiving cell injections ranged from 3 to 90 post-transplantation days (PTD). Control animals who received injections of colloidal carbon were sacrificed three days following intraocular injections. The eyes were enucleated, and the animals sacrificed under deep anesthesia using an intramuscular injection of Ketamine 100 mg/ml at a dose of 90 mg/kg (Quad Pharmaceuticals, Indianapolis, Ind.) and intramuscular Rompun 20 mg/ml at a dose of 8 mg/kg (Xylazine, Mobay Corp., Shawnee, Kans.). The eyes were enucleated and fixed in 6% glutaraldehyde in cacodylate buffer for 24 to 48 hrs. They were then rinsed in buffer and split along the sagittal axis, extending from the cornea to the optic nerve. The hemisected eyes were examined and photographed under a stereomicroscope, and were then embedded in plastic (Eponate 12, Ted Pella, Redding, Calif.). One micrometer ($\mu$m) thick sections were cut and stained with Stevenel Blue (5,6) for light microscopic study. Ultra thin sections were cut with a diamond knife for electron microscopic studies. They were stained with lead acetate (7) and studied under a Zeiss 10 electron microscope operating at 80 kilovolts (kv). Some of the retinas injected with colloidal carbon were dissected free and prepared as flat-mounts in order to better evaluate the extent of diffusion of the injected fluid throughout the host retina.

The intraoperative results from the set of control experiments using colloidal carbon, demonstrated that the carbon is injected precisely into the sub-retinal space. The entire procedure could be viewed directly under the operating microscope. It was possible to see how the needle penetrated the sclera and pushed the retina upward. At that point, the bevel was turned in order to put it in apposition to the retina, at an orientation which assured proper localization of the injected material. At this point, the injection was carried out. As the two microliters of fluid were injected, the colloidal carbon was readily seen spreading over the retinal surface. The material quickly fanned out and covered anywhere from 60° to 180° per injection. The colloidal carbon dramatically illustrates the wide diffusion of the injected fluid over the surface of the host retina. It also serves as a control for the result obtained by transplanting living cells. Access to any portion of the retina, even as far posteriorly as the region around the optic nerve head was possible.

Clinical observations have confirmed the atraumatic nature of this technique. The wound is self-sealing, thus requiring no surgical closure. There was no vitreal loss at the time of injection and post-operative examinations showed no corneal opacities, no lenticular changes, a normal optic nerve head, and an intra-ocular pressure which remained stable throughout. Indirect ophthalmoscopy was negative for signs of hemorrhage, neovascularization, uveitis or ocular infection in the eyes of approximately 100 rats and 2 monkeys transplanted using this procedure.

Histological observations correlated well with those made by biomicroscopy. Sections of eyes injected with a tracer and those injected with suspensions of living human fetal retinal cells showed considerable dispersion of the injected material, which spread onto the outer retinal surface from the subretinal injection point. Colloidal carbon injections dramatically illustrate the vast surface of the host retina which is covered by even a single injection. When a flat mount is made of the same preparation, it dramatically indicates the wide diffusion of the carbon granules throughout the retina. On histological specimens involving colloidal carbon injections, there is clearly intraretinal colloidal carbon materials scattered throughout.

In experiments where living human fetal retinal cells were grafted, the same pattern of distribution was observed as those seen in control injections, where colloidal carbon was introduced into the subretinal space. Typically, the penetration point was marked by comparatively large clusters of cells, which could reach dimensions of 250 micrometers thick and 600 micrometers wide.

The initial retinal transplantation experiments (8) were performed using glass micropipettes attached to a microliter syringe. A preliminary incision was made through the sclera, and the transplant was then performed. This technique, although very effective in the rodent model, proved to be difficult and time consuming with severe limitations on accuracy. Suturing of the minute incision in particular, was associated with a sharp increase in complications, such as retinal detachments subretinal hemorrhages, and formation of intravitreal membranes. A modified approach was developed which avoided suturing (9) and its complications, e.g. decreased the formation of pre-retinal membranes, and sharply reduced the incidence of hemorrhaging. However, the method did not eliminate the associated problems in their entirety. Therefore, a need for devising a more expeditious and efficient means of transplantation became necessary, i.e. a method that would make multi-site grafting into retinas not only possible, but virtually free from surgical complications. It is believed that a quick and atraumatic method could limit the complications, as well as the cellular response. A goal was to formulate a means which would be uncompli- cated and quick, but at the same time guarantee that the cells would be delivered intraretinally, at multiple points, in a safe and reliable manner.

The closed eye method of transplantation is believed to be highly desirable because it avoids the need for surgically opening the eye and thus makes it feasible and practical to perform multiple simultaneous grafts into an intact globe. The procedures, in accordance with the invention, have photographically demonstrated a retinal transplantation. The methods have undergone sufficient laboratory testing to state that the cells are being delivered at the desired subretinal or intraretinal locations under direct visual control by the operator.

The procedure, in accordance with the invention, is believed to be quick and efficient and to provide the added advantage of multi-site delivery of cells over a broad surface area, and thereby to vastly improve the odds for success of the transplantation. Perhaps even more significantly, it is a benign procedure. Because it is quick, there is only a need for brief anaesthesia, to thereby further limit the complication rate. The rapid transplantation of cells also diminishes the risk of infection or post-operative complications. The simplicity of the procedure, an intraocular injection, means that the risk of intraoperative complication should be minimal. The rat model presents an uncomplicated approach. In all the cases performed by or for the rodent and primates (13) there have been no intra-operative or post-operative complications.

When performing these procedures, it is desirable to use different parameters in order to test various experimental paradigms. By allowing controlled penetration of the sub-retinal and retinal spaces this technique does exactly that. The colloidal carbon manifests precise placement of material on a macroscopic and histological level. When using living donor cells, the results shown by histological examination are once again the same successful intraretinal placement of cells. The results, in accordance with the invention, suggest that a reproducible procedure of intraocular cell delivery can be used, that works in the models, and could be used in humans. The procedure is believed to be sufficiently free of complications to be the technique of choice for future transplantation of neural retinal cells into adult hosts.

Because of its technical simplicity and safety, as well as the area of the retina which is covered during its application, it is believed that procedures in accordance with the invention can be easily and effectively performed in a variety of situations. It is believed that the field of retinal transplantation could benefit from such a safe and reliable means of cell placement.

REFERENCES

1. Lazar E and del Cerro M: A new procedure for retinal transplantation, ARVO meeting, Sarasota Fla., May 1990. Invest. Ophthalmol. Vis. Sci. 31:593, 1990 (Abstr.)

2. del Cerro M, Gash DM, Rao GN, Notter MFD, Wiegand SJ, and Ishida No: Intraocular retinal transplants. ARVO Meeting, Sarasota, Fla., May, 1984. Invest: Opthalmol Vis. Sci. 25: 62, 1984 (Abstr.)

3. del Cerro M, Grover DA, Dematte JE, and Williams, WM: Colloidal carbon as a combined ophthalmoscopic and microscopic probe of the retinal-blood barrier integrity. Ophthalmic Res . 17: 34, 1985.

4. Triarhou L. and del Cerro M: Colloidal carbon as a multilevel marker for experimental lesions. Experientia 41; 620,1985.

5. del Cerro M, Cogen M.J., and del Cerro C: An excellent stain for opticalmicroscopy study of plastic embedded tissues. Microscope Acta 83: 5453, 1980.

6. del Cerro M, Standler M, and del Cerro C: High resolution optical microscopy of animal tissues by the use of sub-micrometer thick sections and a new stain. Microscope Acta 83: 117, 1980.

7. Venable, J. and Cogeshall R: A simplified lead citrate stain for use in electron microscopy. J. Cell Biol. 407, 1985.

8. del Cerro M, Gash D.M., Notter M, Rao G.No, Wiegand S, Jiang L, and del Cerro C: Transplanting strips of immature retinal tissue and suspensions of dissociated retinal cells into normal and extensively damaged eyes. Ann of N.Y. Acad of Sci 495: 692, 1986.

9. del Cerro M, Notter M, del Cerro C, Wiegand S, Grover D, and Lazer E (1989) Intraretinal Transplantation for rod-cell replacement in light-damaged retinas. J of Neur. Transpl. 1:1.

10. Lopez R, Gouras P, Brittis M, and Kjeldby H; Transplantation of cultured rabbit retinal epithelium to rabbit retina using a closed eye method, Invest Opthalmol Vis Sci 28: 1131, 1987.

11. Sheedlo H, Li L, and Turner J: Functional and structural characteristic of photoreceptor cells rescued in RPE- cell grafted retinas of RCS dystrophic rats. Exp. Eye Res. 48:841, 1989.

12. Silverman M, and Hughes, S: Transplantation of Photoreceptors to Light-Damaged Retina. Invest Ophthalmol Vis Sci. 30: 1684, 1989.

13. del Cerro M, Lazar E, Grover D, Gallagher M, Sladek C, Chu J, and del Cerro C: Intraocular Transplantation and culture of human embryonic retinal cells. ARVO meeting, Sarasota Fla., May 1990. Invest Ophthalmol. Vis. Sci. 31: 593, 1990 (Abstr.)

We claim:

1. An intraocular delivery and withdrawal instrument comprising:

an elongated handle having a distal end and a proximal end and shaped and dimensioned to be grasped by the hand of a user and an elongated curved frame extending from the distal end of the handle and having a proximal end; and a tip extending from said distal end of the frame;

said frame and tip being shaped and dimensioned for insertion into an orbit along an insertion path around the periphery of the eye so to place said tip adjacent to the retina and pointing in a direction for penetration into the intraocular region of the eye when said tip is moved generally in the medial direction by manipulating said handle.

2. An instrument as in claim 1 including an adjustable collar secured to the instrument to regulate the extent to which said tip penetrates into the intraocular region of the eye.

3. An instrument as in claim 2 in which said tip comprises a 30 gauge needle tip extending at an angle to the distal end of said frame.

4. An instrument as in claim 2 in which said tip comprises a 27 gauge needle tip extending at an angle to the distal end of said frame.

5. An instrument as in claim 2 in which said tip comprises a screw thread and said adjustable collar and has a mating screw thread to allow varying said degree of penetration by the degree to which said screw threads mate.

6. An instrument as in claim 5 in which said adjustable collar is made of a plastic material.

7. An instrument as in claim 5 in which said adjustable collar is made of a metal.

8. A method for delivering a solution to on intraretinal area of an eye in vivo which comprises:

inserting an intraocular delivery and withdrawal instrument into an orbit in an insertion direction which is peripheral to the eye and within the orbit; said instrument comprising an elongated handle having a distal end and a proximal end and shaped and dimensioned to be grasped by the hand of a user and an elongated curved frame extending from the distal end of the handle and having a proximal end; and a tip extending from said distal end of the frame; said frame and tip being shaped and dimensioned for insertion into said orbit in said insertion direction so to place said tip adjacent to the retina and pointing in a direction for penetration into the intraocular region of the eye when said tip is moved generally in the medial direction by manipulating said handle;

penetrating the intraocular area with said tip generally in the medial direction; and transferring solution from the instrument to the intraocular area.

9. The method of claim 8 in which said solution is a pharmaceutical agent.

10. The method of claim 8, wherein the solution is a toxin.

11. A method for withdrawing a biological sample from an intraocular area of an eye in vivo which comprises:

inserting an intraocular delivery and withdrawal instrument comprising an elongated handle having a distal end and a proximal end and shaped and dimensioned to be grasped by the hand of a user and an elongated curved frame extending from the distal end of the handle and having a proximal end; and a tip extending from said distal end of the frame; said frame and tip being shaped and dimensioned for insertion into an orbit along an insertion path around the periphery of the eye so to place said tip adjacent to the retina and pointing in a direction for penetration into the intraocular region of the eye when said tip is moved generally in the medial direction by manipulating said handle; into an orbit in an insertion direction around the periphery of the eye and penetrating the eye generally in the medial direction so as to reach the intraocular area with said tip; and transferring a sample from the intraocular area to the instrument and withdrawing said instrument from the eye.

12. A method as in claim 11 in which said biological sample is a cell.

13. A method as in claim 11 in which said biological sample is intraocular fluid.

14. An intraocular delivery and/or withdrawal instrument comprising:

an elongated handle having a distal end and a proximal end and shaped and dimensioned to be grasped by the hand of a user;

an elongated and curved frame extending from the distal end of the handle and having a distal end; and a tip having a hollow passage therein and extending from said distal end of the frame;

said frame and tip being shaped and dimensioned for insertion into an orbit along an insertion path around the periphery of the eye so as to place said tip adjacent the retina and pointing in the medial direction for penetrating into the intraocular region of the eye upon further manipulation of said instrument; and at least one of:
(i) a feed line which is in selective fluid flow communication with said hollow passage of the tip to deliver material thereto, means for selectively generating a delivery command signal and means responsive to said delivery command signal to deliver a selected quantity of a selected material to said hollow passage; and (ii) an aspiration line which is in selective fluid flow communication with said hollow passage of the tip to aspirate material therefrom, means for selectively generating an aspiration command signal and means responsive to said aspiration command signal to aspirate a selected quantity of material from said hollow passage.

15. An instrument as in claim 14 including both elements (i) and (ii).

16. An instrument as in claim 14 having only element (i) and being free of element (ii).

17. An instrument as in claim 14 having only element (ii) and being free of element (i).

* * * * *